United States Patent
Baucom

(10) Patent No.: US 9,795,617 B2
(45) Date of Patent: Oct. 24, 2017

(54) HORMONE DELIVERY SYSTEM AND METHOD

(71) Applicant: Baucom Institute for Longevity and Life Enhancement, Inc., Overland Park, KS (US)

(72) Inventor: Karan Y. Baucom, Overland Park, KS (US)

(73) Assignee: Baucom Institute for Longevity and Life Enhancement, Inc., Overland Park, KS (US)

( * ) Notice: Subject to any disclaimer, the term of this patent is extended or adjusted under 35 U.S.C. 154(b) by 0 days.

(21) Appl. No.: 15/231,448

(22) Filed: Aug. 8, 2016

(65) Prior Publication Data

US 2016/0346298 A1    Dec. 1, 2016

Related U.S. Application Data

(63) Continuation-in-part of application No. 14/189,801, filed on Feb. 25, 2014, now abandoned, which is a continuation-in-part of application No. 12/818,798, filed on Jun. 18, 2010, now Pat. No. 8,658,628.

(60) Provisional application No. 61/218,301, filed on Jun. 18, 2009.

(51) Int. Cl.
    *A61K 31/56*      (2006.01)
    *A61K 31/57*      (2006.01)
    *A61K 31/565*     (2006.01)
    *A61K 31/568*     (2006.01)

(52) U.S. Cl.
    CPC ............ *A61K 31/57* (2013.01); *A61K 31/565* (2013.01); *A61K 31/568* (2013.01)

(58) Field of Classification Search
    USPC .......................................................... 514/170
    See application file for complete search history.

(56) References Cited

U.S. PATENT DOCUMENTS

| | | |
|---|---|---|
| 4,382,441 A | 5/1983 | Svedman |
| 4,534,468 A | 8/1985 | Nuckols et al. |
| 4,573,606 A | 3/1986 | Lewis et al. |
| 4,816,258 A | 3/1989 | Nedberge et al. |
| 4,900,734 A | 2/1990 | Maxson et al. |
| 5,091,182 A | 2/1992 | Ong et al. |
| 5,288,479 A | 2/1994 | Gorman et al. |
| 5,300,302 A | 4/1994 | Tachon et al. |
| 5,310,082 A | 5/1994 | Coustenoble |
| D352,458 S | 11/1994 | Gray |
| 5,397,776 A | 3/1995 | DeLuca et al. |
| 5,505,959 A | 4/1996 | Tachon et al. |
| 5,609,270 A | 3/1997 | Walker |
| 5,813,785 A | 9/1998 | Baudin et al. |
| 5,897,539 A | 4/1999 | Elliesen et al. |

(Continued)

OTHER PUBLICATIONS

"A Comparison between Oral and Transdermal Hormone Therapy", Compounding Education Resource, vol. VII, Chapter 6 (2008), pp. 1.

(Continued)

*Primary Examiner* — San-Ming Hui
(74) *Attorney, Agent, or Firm* — Law Office of Mark Brown, LLC; Christopher M. DeBacker; Mark E. Brown

(57) ABSTRACT

A hormone delivery system and method are provided for administering bioidentical human hormones using a combination of modalities for the treatment of human physiological conditions.

16 Claims, 2 Drawing Sheets

Hormone Delivery System

(56) References Cited

U.S. PATENT DOCUMENTS

| | | | |
|---|---|---|---|
| 5,922,349 | A | 7/1999 | Elliesen et al. |
| 5,927,548 | A | 7/1999 | Villaveces |
| 5,958,446 | A | 9/1999 | Miranda et al. |
| 6,083,528 | A | 7/2000 | Elliesen et al. |
| 6,098,835 | A | 8/2000 | DeJonge |
| 6,165,491 | A | 12/2000 | Grasset et al. |
| 6,228,852 | B1 | 5/2001 | Shaak |
| 6,507,275 | B2 | 1/2003 | Romano et al. |
| D473,786 | S | 4/2003 | Chue |
| 6,544,553 | B1 | 4/2003 | Hsia et al. |
| 6,561,389 | B1 | 5/2003 | Earle |
| 6,581,797 | B2 | 6/2003 | McKinney, Jr. et al. |
| 6,866,865 | B2 | 3/2005 | Hsia et al. |
| 6,967,194 | B1 | 11/2005 | Matsuo et al. |
| 7,100,797 | B2 | 9/2006 | Kahn et al. |
| 7,101,106 | B1 | 9/2006 | Wiley |
| 7,163,699 | B2* | 1/2007 | Besse ............... A61K 9/145 424/456 |
| 7,186,706 | B2 | 3/2007 | Rosario-Jansen |
| 7,204,391 | B2 | 4/2007 | Toker |
| D543,120 | S | 5/2007 | Coe et al. |
| 7,449,310 | B2 | 11/2008 | Nagaraja et al. |
| 8,658,628 | B2 | 2/2014 | Baucom |
| 2002/0142028 | A1 | 10/2002 | Elliesen et al. |
| 2007/0049567 | A1* | 3/2007 | Wiley ............... A61K 9/0014 514/170 |
| 2008/0226703 | A1 | 9/2008 | Sacks et al. |
| 2010/0324006 | A1 | 12/2010 | Baucom |
| 2013/0129818 | A1 | 5/2013 | Bernick et al. |
| 2013/0338122 | A1 | 12/2013 | Bernick et al. |

OTHER PUBLICATIONS

"BioResponse DIM Offers Superior Safety, Stability, Dosage and Efficacy", BioResponse Nutrients, Retrieved online Jun. 18, 2010: www.bioresponse.com, 3.

"International Search Report and Written Opinion", PCT/US2015/017555, May 28, 2015.

"Postmenopausal Estrogen Therapy: Route of Administration and Risk of Venous Thromboembolism", The American College of Obstetricians and Gynecologists, Committee Opinion No. 556 (Apr. 2013, Reaffirmed 2015), pp. 1-4.

"Risks and Benefits of Estrogen Plus Progestin in Healthy Postmenopausal Women: Principal Results From the Women's Health Initiative Randomized Controlled Trial", Writing Group for the Women's Health Initiative Investigators; Journal of the American Medical Association, vol. 288, No. 3, pp. 321-333, Jul. 17, 2002.

"Take comfort in her protection", brochure: Micronized Prometrium Progesterone, USP—retrieved Mar. 16, 2009.

Transdermal Estrogen and Micronized Progesterone: A First-line Hormone Therapy Option, Society of Obstetrics and Gynaecologiests of Canada (SOGC), Jun. 2012, pp. 1-2.

Allen, "Oestrogen and Progestogen for HRT", www.patient.co.uk/medicine/oestrogen-and-progestogen-for-hrt, Feb. 1, 2013.

Armstrong, "ACOG Guidlines on Noncontraceptive Uses of Hormonal Contraceptives", American College of Obstetrics and Gynecologists, Obstetrics & Gynecology, Jan. 2010, Jan. 2010, 1-9.

Briden, "The Crucial Difference Between Progesterone and Progestins", Lara Briden's Healthy Hormone Blog, Oct. 6, 2015.

Cameron, et al., "Continuous transdermal oestrogen and interrupted progestogen as a novel bleed-free regimen of hormone replacement therapy for postmenopausal women", British Journal of Obstetrics and Gynaecology, vol. 104, Issue 10, Oct. 1997, pp. 1184-1190.

Campagnoli, et al., "Progestins and progesterone in hormone replacement therapy and the risk of breast cancer", Journal of Steroid Biochemistry and Molecular Biology, Jul. 2005, vol. 96, Issue 2, 95-108.

Canonico, et al., "Hormone Therapy and Venous Thromboembolism Among Postmenopausal Women: Impact of the Route of Estrogen Administration and Progestogens: The ESTHER Study", Circulation, vol. 115, pp. 840-845, Feb. 20, 2007.

Conaway, "Bioidentical Hormones: An Evidence-Based Review for Primary Care Providers", The Journal of the American Osteopathic Association, Mar. 2011, vol. 111, 153-164.

De Villiers, et al., "Global Consensus Statement on Menopausal Hormone Therapy", Climacteric, vol. 16, No. 2, Apr. 2013, pp. 203-204.

Di Carlo, et al., "Transdermal estradiol and oral or vaginal natural progesterone: bleeding patterns", Climacteric 2010, 13:442-446.

Faloon, "Surprise Findings in Estrogen Debate", Life Extension Magazine, Nov. 2013, Nov. 2013, pp. 7-20.

Feeley, et al., "Hormone replacement therapy and the endometrium", Journal of Clinical Pathology, vol. 54, Issue 6, Jun. 2001, 435-440.

French, "Dysmenorrhea", American Family Physicians, vol. 71, No. 2, Jan. 15, 2005, 285-291.

Fugh-Berman, et al., "Bioidentical Hormones for Menopausal Hormone Therapy: Variation on a Theme", Journal of General Internal Medicine, Jul. 2007, vol. 22, Issue 7, 1030-1034.

Gelfand, et al., "Abstract of: Clinical assessment and quality of life of postmenopausal women treated with a new intermittent progestogen combination hormone replacement therapy: a placebo-controlled study", Menopause, vol. 10, Issue 1, Jan. 2003, 29-36.

Google, "Google image search for "graphs on the menstrual cycle"", https://www.google.com/search?noj=1&q=graphs%20on%20the%20menstrual%20cycle&um=1&ie=UTF-8&hl=en&tbm=isch&source=og&sa=N&tab=wi&ei=F68XUtrlHqW42AWCjoGgCw&biw=1440&bih=770&sei=Ga8XUtG4F6ed2gXzyoCoCQ.

Holtorf, "The Bioidentical Hormone Debate: Are Bioidentical Hormones (Esradiol, Estriol, and Progesterone) Safer or More Efficacious then Commonly Used Synthetic Versions in Hormone Replacement Therapy?", Postgraduate Medicine, vol. 121, Issue 1, Jan. 2009, 1-12.

L'Hermite et al., "Could transdermal estradiol + progesterone be a safer postmenopausal HRT? A review", Maturitas, vol. 60, 2008, 185-201.

Marsden, "Bioidentical Hormone Replacement: Guiding Principles for Practice", Natural Medicine Journal, vol. 2, Issue 3 (Mar. 2010), pp. 1-10.

Mead, "Estrogen Dominance", Retrieved online May 26, 2010, www.labrix.com, 1 of 1.

University of Maryland Medical Center, "Menstrual Disorders", https://umm.edu/health/medical/reports/articles/menstrual-disorders, Sep. 26, 2012, 1-24.

Moskowitz, "A Comprehensive Review of the Safety and Efficacy of Bioidentical Hormones for the Management of Menopause and Related Health Risks", Alternative Medicine Review, vol. 11, No. 3 (Sep. 2006), pp. 208-223.

Nasir, et al., "Management of Pelvic Pain from Dysmenorrhea or Edometriosis", The Journal of the American Board of Family Practice, vol. 17, No. Supp 1, Nov. 1, 2004, S43-S47.

North American Menopause Society, "Estrogen and progestogen use in postmenopausal women: 2010 position statement of the North American Menopause Society", Menopause, vol. 17, No. 2, Mar. 2010, 242-55.

North American Menopause Society, "Recommendations for estrogen and progestogen use in peri- and postmenopausal women: Oct. 2004 position statement of the North American Menopause Society", Menopause, vol. 11, No. 6, Oct. 2004, 589-600.

North American Menopause Society, "Role of progestogen in hormone therapy for postmenopausal women: position statement of the North American Menopause Society", Menopause, vol. 10, No. 2, Feb. 2003, 113-132.

North American Menopuase Society, "Estrogen and progestogen use in peri- and postmenopausal women: Mar. 2007 position statement of the North American Menopause Society", Menopause, vol. 14, No. 2, Mar. 2007, 168-182.

Novogyne Pharmaceuticals, "Dialogues in Menopause Management", Jan. 2012.

Oger, et al., "Differential effects of oral and transdermal estrogen/progesterone regimens on sensitivity to activated protein C among

(56) References Cited

OTHER PUBLICATIONS postmenopausal women: a randomized trial", Arterioscler Thromb Vasc Biol, 23(9), Sep. 1, 2003, 1671-6.
Osayande, et al., "Diagnosis and Initail Management of Dysmenorrhea", American Family Physician, Mar. 1, 2014; 89 (5), Mar. 1, 2014, 341-346.
Scarabin, et al., "Effects of Oral and Transdermal Estrogen/Progesterone Regimens on Blood Coagulation and Fibrinolysis in Postmenopausal Women: A Randomized Controlled Trial", Arterioscler Thromb Vasc Biol, vol. 17, 1997, 3071-3078.
Schwartz, et al., "The Truth About Hormone Therapy", http://online.wsj.com/article/SB123717056802137143.html, Mar. 16, 2009, 1-2.
Society for Endocrinology, "You & Your Hormones: Progesterone", http://www.yourhormonesinfo/Hormones/Progesterone.aspx, Jan. 2012.
Spencer, et al., "Effects of Oral and Transdermal 17B-Estradiol With Cyclical Oral Norethindrone Acetate on Insulin Sensitivity, Secretion, and Elimination in Postmenopausal Women", Metabolism, vol. 49, No. 6, Jun. 2000, 742-747.
Sturdee, et al., "The endometrial reponse to sequential and continuous combined oestrogen-progestogen replacement therapy", British Journal of Obstetrics and Gynaecology, vol. 107, Issue 11, Nov. 2000, pp. 1392-1400.
University Gyn Oncology, "Gyn Oncology Update: Hormone Replacement Therapy", http://www.universitygynoncology.org/lib/tile/manager/Spring_2013_GOU.pdf, Spring 2013.
Vashisht, et al., "A Study to Look at Hormonal Absorption of Progesterone Cream Used in Conjunction with Transdermal Estrogen", Gynecological Endocrinology, 2005, vol. 21(2), pp. 101-105, Aug. 2005.
Whitehead, et al., "Absorption and metabolism of oral progesterone", British Medical Journal, Mar. 22, 1980, pp. 325-827.
Wikipedia, "Menstrual Cycle", http://en.wikipedia.org/wiki/Menstrual_cycle, pp. 1-9.
Wiley, et al., "Sex, Lies, and Menopause: The Shocking Truth About Hormone Replacement Therapy", William Morrow, 2003., pp. 199-208, Appendix II.
Woo, et al., "New Strategies to Treat Primary Dysmenorrhea", Clinical Advisor, Nov. 2010 Issue, Nov. 2010, 1-4.
Zuckerman, et al., "The hormone replacement therapy market for the treatment of menopausal symptoms in the US", Erial, NJ: inThought Research, 2013, pp. 1-21.
"Flowchart showing Nutritional Influences on Estrogen Metabolism", Advanced Nutrition Publications, 2001, Figure 1.
"Flowchart showing the Steroidogenic Pathways", Genova Diagnostics, Aug. 22, 2007.
"Women's Hormonal Health: Understanding Estrogen Metabolism", Genova Diagnostics, 2007, pp. 1-2.
Higdon, et al., "Indole-3-Carbinol", Oregon State University Micronutrient Information Center, Dec. 2008, pp. 1-15.
Lee, "DIM (Di-Indoly Methane) for Natural Protection from Estrogen's Effects", NaturoDoc, 2010, pp. 1-6.
Michnovicz, "Abstract of Changes in levels of urinary estrogen metabolites after oral indole-3-carbinol treatment in humans", J Natl Cancer Inst. May 21, 1997; 89(10):718-23, pp. 1-2.

\* cited by examiner

HORMONE DELIVERY SYSTEM AND METHOD

CROSS-REFERENCE TO RELATED APPLICATIONS

This application is a continuation-in-part of and claims priority in U.S. patent application Ser. No. 14/189,801, filed Feb. 25, 2014, which claims priority in and is a continuation-in-part of U.S. patent application Ser. No. 12/818,798, filed Jun. 18, 2010, now U.S. Pat. No. 8,658,628, issued Feb. 25, 2014, which claims priority in U.S. Provisional Patent Application No. 61/218,301, filed Jun. 18, 2009, both of which are incorporated herein by reference.

BACKGROUND OF THE INVENTION

1. Field of the Invention

The present disclosed technology relates generally to the administration of human hormones, and in particular to various delivery methods of bioidentical hormone formulations.

2. Description of the Related Art

Hormones are chemical substances produced by cells and organs of the body that affect organs and body systems. Hormones are important for cardiovascular maintenance, musculature, the skeletal system, and cognitive functioning. The body's production of hormones and how the body reacts to hormones affect the well being of individuals and the aforementioned body systems.

The body has three general categories of sex hormones; androgens (ex. testosterone), estrogens (estradiol and estrone), and progestagens (ex. progesterone). Particular female sex hormones and their associated organs are, for example, testosterone (ovaries), estrone and estradiol (ovaries), and progesterone (ovaries and placenta). Testosterone promotes the growth and maintenance of the skeletal system, musculature, and connective tissues, to name a few. Estradiol and estrone principally affect the female reproductive system. Progesterone affects the female menstrual cycle, and maintenance of pregnancy. Hormone deficiencies caused by aging, disease states, exogenous and endogenous environmental conditions, and certain prescribed medications can upset the balance of sex hormones within the body and affect general well being, lifespan, quality of life, and may lead to disease states as well. Therefore, in order to counter the negative effects of hormone deficiencies, patients are often prescribed hormone replacement therapy (HRT) by their treating physicians.

HRT is a system of treatment using either synthetic sex hormones, or bioidentical sex hormones to treat the effects of diminished sexual hormone levels in peri-menopausal, menopausal, and post-menopausal women. Synthetic sex hormones are the predominant type of hormone proscribed in HRT. The types of techniques used in HRT to deliver sex hormones include pills, capsules, gels, creams, patches and troches. Use of synthetic sex hormones in HRT comes with significant problems such as heart problems, cancers and other undesirable side effects. Furthermore, the type and amount of sex hormone administered is limited by dosing regimens associated with the available delivery techniques. Patient selection of desired delivery techniques and source of sex hormones will increase the effectiveness of therapy and compliance. Moreover, the ability of a physician to tailor the amount of sex hormone delivered with each dosing regime will increase the effectiveness of HRT. Therefore, there is a need for a system of HRT that avoids the undesirable side-effects of synthetic hormone treatments, and that provides the patient with a range of techniques for administering the hormones to maximize well being and maintenance of body systems.

Heretofore there has not been available a hormone delivery system with the advantages and features of the disclosed technology.

SUMMARY OF THE INVENTION

A hormone delivery system is disclosed providing for administration of bioidentical human hormones using a combination of modalities for the treatment of human physiological conditions where treatment by hormone therapy is indicated. Bioidentical estrogen, progesterone and androgen preparations may be administered individually, or in combination to a patient using one or more modalities such as transdermal absorption or ingestion. The hormone delivery system can be used to treat pre-menstrual tension syndrome, peri-menopause, menopause, post-menopause, progesterone deficiency, estrogen dominance, libido issues, and birth control.

When using bioidentical hormones for the efficacy of treating peri-menopausal and menopausal women, it is best to simulate the natural menstrual cycle. Utilizing estrogen throughout the 28 day cycle (from day 1 to day 28), and introducing progesterone as early as day 10 or as late as day 14, can produce these results. During tests, this resulted in producing a period, primarily during the last 5 days of the month. The progesterone portion of the cycle dominates the shedding or secretory phase of the process. The intensity would vary depending on the dosage of estrogen based upon its proliferation of the endometrial lining.

A "steady state" occurs where there is little or no bleeding during the secretory phase. This is based upon the endometrial layer being so scant that the progesterone does not induce bleeding. Previously it was a concern that the endometrial layer would remain and become exposed to the estrogenic component. However, as long as progesterone is also being introduced, there is a ratio that results in an equilibrium wherein the endometrial layer neither grows nor sheds.

Estrogen dominance can occur when large doses of estrogen are predominantly utilized without being balanced out with progesterone. Inducement of the cycle with the use of progesterone with the intact uterus can help to prevent endometrial hyperplasia. Therefore, any female patient utilizing estrogen in a delivery system should also balance that with progesterone.

The type of progesterone used is also important. Oral micronized progesterone and various progestogens are available. Progestogens include natural progesterone and synthetic progestins.

Existing solutions provided by physicians do not incorporate both estrogen and progesterone in a physiological manner that can be simply dosed to the patient. A preferred solution would include a distribution system that is pre-packaged and self-explanatory to the patient.

An embodiment of the present invention presents a hormone delivery system (HDS) which provides the hormones to the patient in a biologically, physiological manner which simulates the menstrual cycle. These hormones can be presented in a number of ways. Transdermal applications include patches, gels, creams, or some combination thereof. The estrogen must be presented in a transdermal application, but the progesterone could also be presented orally, such as in a capsule.

If issues arise, such as breast tenderness and extensive bleeding, this can alert the patient and the treating physician to mechanical causes (e.g. fibroids, endometriosis, or andenomyosis) or that the estrogenic component is being given in such a way that, combined with the patient's own endogenous estrogens, have created estrogen dominance. The remedy is to decrease the estrogenic component of the HDS.

The advantage of the present invention is to provide an HDS that is modifiable by the treating physician by adjusting the dosages. As an example, using gels and creams, the physician can prescribe 25 milligrams per application. The hormones being provided through the HDS are well suited for these variations.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the disclosed technology are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art how to variously employ the disclosed technology in virtually any appropriately detailed structure.

II. Embodiment or Aspect of the Hormone Delivery System

The hormone delivery system embodying the principles of the disclosed technology provides for administration of compositions containing bioidentical human hormones in an amount sufficient to provide therapeutic effect, using a combination of modalities, for the treatment of human physiologic conditions. Examples of specific bioidentical hormones which may be used include, but are not limited to estrogens (estrone, estradiol), progesterone, and androgens (testosterone, androstenedione, dihydrotestosterone (DHT), dehydroepiandrosterone (DHEA)) isomers and derivatives thereof, and combinations thereof. Examples of specific modalities which may be used include, but are not limited to topical preparations (gel, cream), ingested articles (tablet, lozenge, capsule, troches), and articles for transdermal absorption of hormone preparations (transdermal patch, impregnated matrices). The type and amount of hormones involved in the various bioidentical human hormone compositions, and the modalities used varies depending independently, or in conjunction with, the physiologic sequence based on the normal menstrual cycle pattern, and specific clinical syndromes involved. A single bioidentical hormone or a combination of bioidentical hormones may be used with any particular modality.

The hormone delivery system may be used for the treatment of conditions related to hormone imbalances or deficiencies where treatment by hormone therapy is indicated. For example, the types of conditions for which the hormone delivery system may be used include, but are not limited to: pre-menstrual tension syndrome; peri-menopause, menopause, post-menopause; progesterone deficiency; estrogen dominance; and libido issues. Additional treatment measures include providing birth control. In conjunction with treatments using estrogens, the hormone delivery system is used in conjunction with indole-3-carbinol, di-indole methane, or flax seed to protect biochemically from hydroxylation of estrogen.

III. Alternative Embodiment or Aspect of the Hormone Delivery System 2

Figure 1:
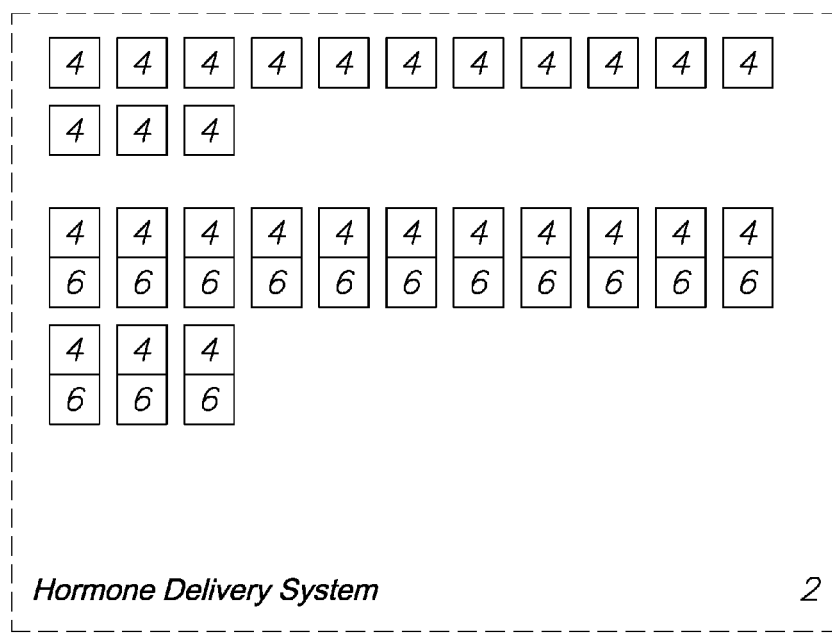
FIG. 1 box diagram illustrating the relationship between various elements of an embodiment of the present invention.

As shown in FIG. 1, a pre-packaged hormone delivery system (HDS) 2 comprising another embodiment or aspect of the disclosed technology can be used for treating perimenopause, menopause and post-menopause. The bioidentical human hormones estrogens 4 (estrone, estradiol), progesterone 6 using a combination of modalities mentioned above are administered to a patient in a sequential format following the human physiological twenty-eight day menstrual cycle as diagrammed in FIG. 2. Any combination of patches, capsules and other types of delivery systems can be utilized, provided the menstrual cycle is simulated.

Various combinations of estrogen/progesterone can be administered as a cream with suitable proportions and dosage ranges.

The present invention is pre-packaged for clinical efficiency. This ensures the proper dosage without requiring the physician to mix and match the estrogen and the progesterone doses separately. The hormones being applied through the delivery system are FDA approved in a therapeutic fashion for hormone replacement therapy. Examples include 17-B estradiol, progesterone, progestogens, and progestins.

The delivery system is intended for involving estrogen throughout the standard menstrual cycle (from day one through the entire month) and utilizing progesterone as early as day ten or as late as day fourteen. This ensures progesterone is initiated in addition to the estrogen for the remainder of the cycle. This results in a period primarily during the final 5 days of the month based upon the dosage of estrogen, as it is the estrogen component that proliferates the endometrial lining.

Figure 2:
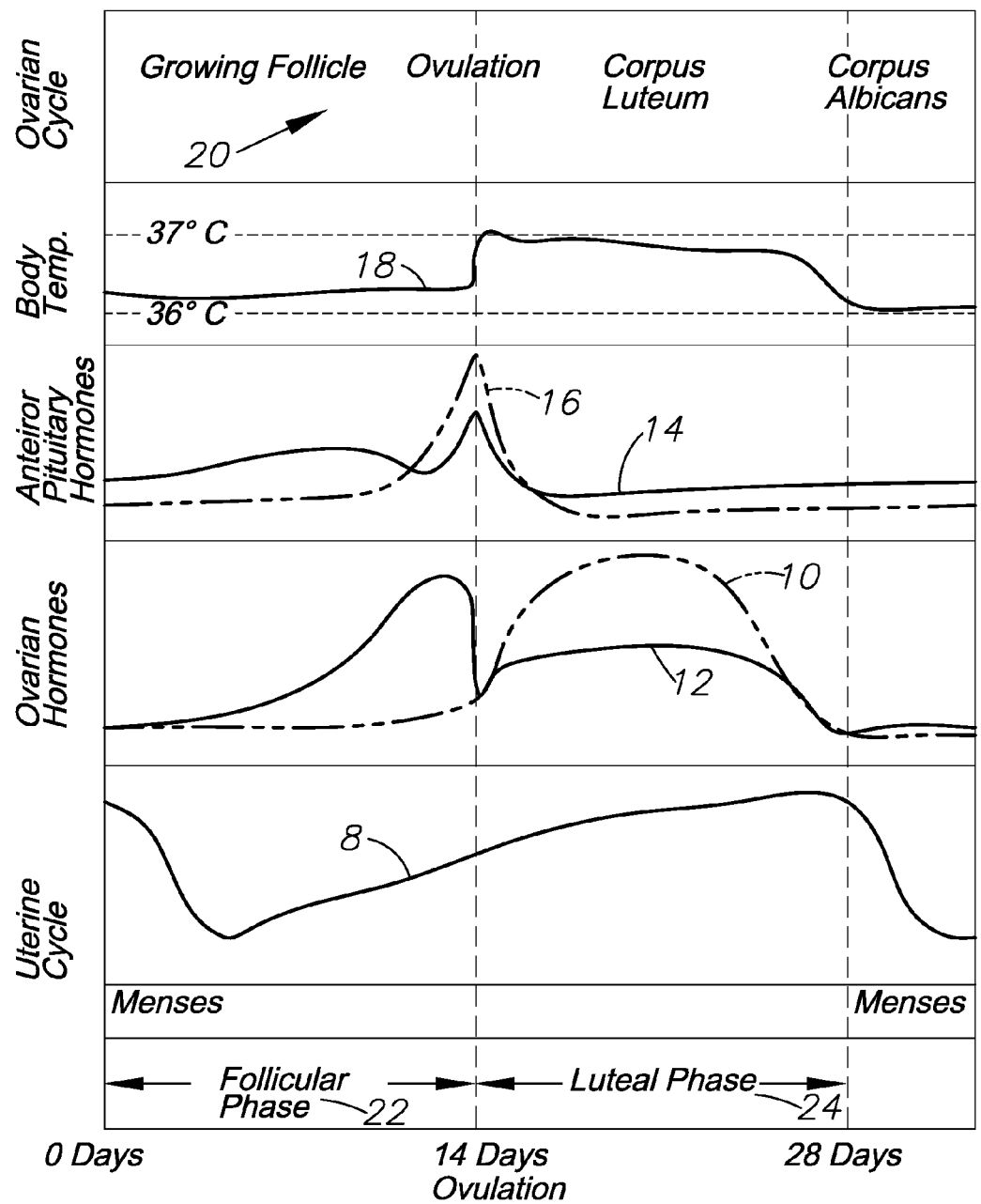
FIG. 2 is a chart diagramming a timeline based upon various elements and aspects of the present invention.

The shedding of secretory phase, as shown in FIG. 2, is under the dominance of the progesterone portion of the cycle, initiating the menstrual cycle. The bleeding can be controlled based upon how much estrogen is provided and as to how the endometrial lining responded in its proliferation.

The present invention simulates the physiological menstrual cycle as its template, mimicking the normal rhythmic delivery of the sex steroids. FIG. 2 illustrates this in some detail. The graph element 8 illustrates the uterine cycle; namely, the thickness of the endometrial lining during a typical cycle. Element 10 graphs the progesterone hormone level over that cycle, and element 12 illustrates the estradiol level. Similarly, element 14 illustrates the follicle-stimulating hormone (FSH) while element 16 represents the lutenizing hormone (LH). Body temperature along the cycle is illustrated at element 18. The phases of the cycle are listed at 20. The follicular phase is represented at 22 and the luteal phase at 24.

Summarizing, the hormone delivery system of this embodiment provides estrogen and progesterone replacements. The estrogen would be provided via a topical solution such as a gel or cream, but the progesterone could be provided either through a micronized oral progesterone (e.g., capsule, sub lingual, troche, or pill) or through a topical, preferably vaginal, gel, cream, or transdermal spray.

Dosage ranges for the progesterone can range between 20 milligrams through 300 milligrams.

The 28 day cycle may initiate the progesterone component as early as day 10 or as late as day 14. The component is used cyclically in association with continuous bioidentical estrogen.

By way of example and without limitation, estrogen can be administered as a patch, gel or cream in suitable dosages of, for example, 0.25 mg, 0.375 mg, 0.5 mg, 0.75 mg and 1.0 mg. Progesterone can be administered as a patch, gel, cream, capsule or sublingual in suitable dosages of, for example, 25 mg, 50 mg, 75 mg, 100 mg, 200 mg and 300 mg. Di-indole methane/3-indole carbinol (Dim/3IC) can be administered as 400 mg tablets or gels. However, estrogen-dominant patients should only be given progesterone during days 1-25 of their menstrual cycles. If any estrogen is used, an option is to utilize 3IC/Dim for pathway protection for increasing 2-meo/2 hydroxylation excretion. It is generally important for the patient to excrete estrogen.

Support for the concepts disclosed herein can be found in the following list of references, where are incorporated herein by reference:

Cameron, Sharon T. et al., *Continuous Transdermal Oestrogen and Interrupted Progestogen as a Novel Bleed-Free Regimen of Hormone Replacement Therapy for Postmenopausal Women*, British Journal of Obstetrics and Gynaecology, Oct. 1997, Vol. 104 pp. 1184-1190.

Campagnoli, C. et al., *Progestins and Progesterone in hormone Replacement Therapy and the Risk of Breast Cancer*, Journal of Steroid Biochemistry and Molecular Biology, Jul. 2005 Vol. 96 No. 2 pp. 95-108.

*Role of Progestogen in Hormone Therapy for Postmenopausal Women: Position Statement of the North American Menopause Society* (Retired), Menopause: The Journal of the North American Menopause Society, Vol. 10 No. 2, pp. 113-132.

William Faloon, *Surprise Findings in Estrogen Debate*, Life Extension Magazine, Nov. 2013.

IV. Alternative Embodiment Hormone Delivery System for Treatment of Libido issues with Menopause An alternative embodiment of the present invention seeks to treat libido issues, specifically but not exclusively during menopause, by providing a combination of estrogen, testosterone, and progesterone to the patient. Testosterone will be prescribed to the patient from day 7 through day 20 of the 28 day cycle.

V. Alternative Embodiment Hormone Delivery System for Treatment of PMDD, PMS, and Estrogen Dominance An alternative embodiment of the present invention uses a combination of estrogen and progesterone at dosages of 25 mg, 50 mg, 100 mg, or 200 mg to treat PMDD, PMS, and/or estrogen dominance. This combination can also be used to treat insomnia in menopausal and post-menopausal women.

VI. Alternative Embodiment Hormone Delivery System for Treatment of Vaginal Dryness, Atrophy, and/or Dyspareunia An alternative embodiment of the present invention uses a combination of estradiol and testosterone to treat vaginal dryness, atrophy, and/or dyspareunia. A combination of 2 mg/ml of estradiol and 5 mg/ml of testosterone is applied intravaginally 2-3 times per week. This is not to be used for menopausal systemic therapy.

VII. Alternative Embodiment Hormone Delivery System for Treatment of Severe Menstrual Pain (e.g. Dysmenorrhea and Premenstrual Dysmorphic Syndrome ("PMDS"))

An alternative embodiment of the present invention uses a bio-identical progesterone provided to the patient for a twenty-five (25) day cycle during a month. Bio-identical estrogen may also be sequentially added during this process. These applications of bio-identical hormones can be used to treat Dysmenorrhea and PMDS. Dysmenorrhea is the medical term for the painful cramps that may occur immediately before or during the menstrual cycle.

There are two types of Dysmenorrhea: primary and secondary. Primary dysmenorrhea is another name for common menstrual cramps. The pain or cramping is felt in the lower abdomen of back. The pain or cramping starts shortly before or at the onset of the period and may continue for one to three days. It can be associated with premenstrual dysmenorrhea syndrome, where a more severe form of dysmenorrhea can occur. Symptoms associated with this form can be depression, anxiety, mood disorders, irritability occurring at least two weeks prior to menses.

Secondary dysmenorrhea is pain caused by a disorder in the woman reproductive organs. These cramps begin earlier with the menstrual cycle and last longer. Symptoms of each include: aching pain in the abdomen (sometimes severe); pressure in the abdomen; pain in the hips, lower back, and inner thighs due to cramping; upset stomach; and loose stools.

Progesterone for this purpose may be transmitted transdermally or orally. The oral distribution of the progesterone could be combined with estrogen in a sequential format. In a preferred embodiment, a delivery system would include a package with 25 pills or some other oral administration of the hormones. These would be taken by the patient in sequential order, and estrogen may be added to the same pills such that estrogen is introduced sequentially as well.

Bio-identical Progesterone may be provided in a pre-packaged delivery system sequentially dated for a thirty-day cycle, where the progesterone is provided alone for the first 25 days of the thirty-day cycle. Alternatively, bio-identical progesterone may be provided for days 1-30 of the 30 day cycle and bio-identical estrogen introduced in a separate modality (e.g. a separate pill or other modality) from days 14-30. Alternatively, bio-identical estrogen may be provided for days 1-30 of the 30 day cycle and bio-identical progesterone introduced as early as day 10 or as late as day 14 through the end of the 30-day cycle. The treatment should fit the needs of the patient. The pre-packaged hormones are labeled and produced in such a way as to help the patient maintain an orderly cycle of taking the correct hormones on the correct day of the cycle.

It will be appreciated that the components of the hormone delivery system can be used for various other applications. Moreover, the hormone delivery system can be fabricated in various sizes and from a wide range of suitable materials, using various manufacturing and fabrication techniques It is to be understood that while certain aspects of the disclosed technology have been shown and described, the disclosed technology is not limited thereto and encompasses various other embodiments and aspects.

Having thus described the invention, what is claimed as new and desired to be secured by Letters Patent is:

1. A pre-packaged hormone delivery system comprising:
   a pre-packaged, predetermined quantity of bio-identical progesterone, wherein said bio-identical progesterone is provided in a modality selected from the list comprising: a transdermal application; and an oral modality;
   a pre-packaged, predetermined quantity of indole provided sequentially in a 400 mg dosage in a modality selected from the list comprising: a transdermal application; and an oral modality;

said bio-identical progesterone delivered to a patient in predetermined doses during a predetermined cycle; and said bio-identical progesterone configured to treat a menstrual disorder.

2. The pre-packaged hormone delivery system of claim 1, wherein said predetermined cycle is a 25-day cycle, and wherein said menstrual disorder is selected from the list comprising: premenstrual syndrome; and menstrual cramp dysmenorrhea.

3. The pre-packaged hormone delivery system of claim 1, further comprising:

a pre-packaged, predetermined quantity of bio-identical estrogen, wherein said bio-identical estrogen is provided in a modality selected from the list comprising: an oral pill; a sublingual pill; a patch; or a gel;

wherein said bio-identical estrogen is delivered sequentially with said bio-identical progesterone; and wherein said estrogen and said progesterone are contained in separate modalities.

4. The pre-packaged hormone delivery system of claim 3, further comprising:

wherein said estrogen is provided in a thirty-day cycle and is packaged accordingly within said pre-packaged delivery system;

wherein said progesterone is packaged such that it is introduced between days ten and fifteen of said thirty-day cycle.

5. The pre-packaged hormone delivery system of claim 3, further comprising:

wherein said progesterone is provided in a thirty-day cycle and is packaged accordingly within said pre-packaged delivery system; and wherein said estrogen is packaged such that it is introduced between days ten and fifteen of said thirty-day cycle.

6. The pre-packaged hormone delivery system of claim 3, wherein said bio-identical progesterone is derived from plants.

7. The pre-packaged hormone delivery system of claim 3, wherein said bio-identical estrogen is derived from plants.

8. The pre-packaged hormone delivery system of claim 3, wherein said menstrual disorder is associated with peri-menopause, menopause, and post-menopause.

9. The pre-packaged hormone delivery system of claim 3, wherein said menstrual disorder is polycystic ovary syndrome.

10. The pre-packaged hormone delivery system of claim 3, wherein said bio-identical progesterone is delivered in a dosage amount selected from the list comprising: 0.025 mg; 0.0375 mg; 0.05 mg; 0.075 mg; 0.25 mg; 0.375 mg; 0.75 mg; and 1.0 mg.

11. The pre-packaged hormone delivery system of claim 1, further comprising:

wherein said bio-identical progesterone is delivered in a dosage amount selected from the list comprising: 20 mg; 30 mg; 50 mg; 100 mg; 200 mg; and 300 mg; and wherein said menstrual disorder comprises insomnia symptoms.

12. The pre-packaged hormone delivery system of claim 3, wherein said bio-identical estrogen is delivered in a dosage amount selected from the list comprising: 0.025 mg; 0.0375 mg; 0.05 mg; 0.075 mg; and 0.1 mg.

13. The pre-packaged hormone delivery system of claim 1, wherein said indole is selected from the list of indoles comprising: Di-indole methane and 3-indole carbinol.

14. The pre-packaged hormone delivery system of claim 3, further comprising:

a pre-packaged, predetermined quantity of bio-identical testosterone, wherein said bio-identical testosterone is provided in a modality selected from the list comprising:

transdermally; and intramuscularly;

wherein said bio-identical testosterone is delivered sequentially with said bio-identical progesterone and said bio-identical estrogen; and wherein said bio-identical testosterone is provided from day 7 through day 20 of a 28-day cycle.

15. The system of claim 13, further comprising:

wherein said indole is applied in combination with the progesterone only during days 10-31 of each cycle; and wherein the daily dosages of said indole are selected from a list of dosages comprising:

100 mg; 200 mg; and 400 mg.

16. The system of claim 13, wherein said indole is applied daily throughout the entire cycle and wherein said daily dosages of said indole are selected from a list of dosages comprising: 100 mg; 200 mg; and 400 mg.

\* \* \* \* \*